US009042956B2

(12) United States Patent
Clare et al.

(10) Patent No.: US 9,042,956 B2
(45) Date of Patent: May 26, 2015

(54) SYSTEM AND METHOD FOR POWER-EFFICIENT TRANSMISSION OF EMG DATA

(71) Applicant: Tech Team LLC, Palo Alto, CA (US)

(72) Inventors: Christopher R. Clare, Los Altos Hills, CA (US); Denise F. Gottfried, Woodside, CA (US); Jonathan Gottfried, Woodside, CA (US)

(73) Assignee: TECH TEAM LLC, Palo Alto, CA (US)

( * ) Notice: Subject to any disclaimer, the term of this patent is extended or adjusted under 35 U.S.C. 154(b) by 0 days.

(21) Appl. No.: 14/285,363

(22) Filed: May 22, 2014

(65) Prior Publication Data

US 2015/0051471 A1    Feb. 19, 2015

Related U.S. Application Data

(63) Continuation of application No. 13/486,257, filed on Jun. 1, 2012, now Pat. No. 8,768,428.

(60) Provisional application No. 61/492,136, filed on Jun. 1, 2011.

(51) Int. Cl.
| | |
|---|---|
| *A61B 5/04* | (2006.01) |
| *A61B 5/22* | (2006.01) |
| *A61B 5/0492* | (2006.01) |
| *A61B 5/11* | (2006.01) |
| *A61B 5/00* | (2006.01) |
| *A61N 1/00* | (2006.01) |

(52) U.S. Cl.
CPC ............. *A61B 5/224* (2013.01); *A61B 5/0492* (2013.01); *A61B 5/1107* (2013.01); *A61B 5/742* (2013.01)

(58) Field of Classification Search
CPC ..................... A61B 5/04017; A61B 5/042438
USPC ................... 600/372, 382, 384, 386–393; 607/115–116
See application file for complete search history.

(56) References Cited

U.S. PATENT DOCUMENTS

| 4,811,742 A | 3/1989 | Hassel et al. |
| 5,277,197 A | 1/1994 | Church et al. |
| 5,722,420 A | 3/1998 | Lee |

(Continued)

OTHER PUBLICATIONS

European search report and written opinion dated Nov. 5, 2014 for EP Application No. 12794026.

(Continued)

*Primary Examiner* — Joseph Stoklosa
*Assistant Examiner* — Brian M Antiskay
(74) *Attorney, Agent, or Firm* — Wilson Sonsini Goodrich & Rosati

(57) ABSTRACT

The system for displaying muscle force data includes a wearable patch and a remote visual display. The wearable patch carries electrodes suitable for sensing electromyographic signals on the skin of the patient. The patch carries circuitry which converts the detected electromyographic signal to a digital output which can be transmitted to the remote visual display. The circuitry relies on filtering to produce a usable digital signal at very low power consumption. The transmitted signal can be used to drive a variety of visual displays, including a conventional hand-held personal communicators and entertainment devices which had been programmed to suitably process the visual display.

15 Claims, 8 Drawing Sheets

(56) References Cited

U.S. PATENT DOCUMENTS

| | | |
|---|---|---|
| 6,238,338 B1 | 5/2001 | Deluca et al. |
| 6,265,978 B1 | 7/2001 | Atlas |
| 6,440,067 B1 | 8/2002 | Deluca et al. |
| 6,643,541 B2 | 11/2003 | Mok et al. |
| 6,984,208 B2 | 1/2006 | Zheng |
| 7,152,470 B2 | 12/2006 | Impio et al. |
| 7,359,750 B2 | 4/2008 | Song et al. |
| 7,369,896 B2 | 5/2008 | Gesotti |
| 7,563,234 B2 | 7/2009 | Cordo |
| 7,602,301 B1 | 10/2009 | Stirling et al. |
| 7,613,510 B2 | 11/2009 | Rentea et al. |
| 7,628,750 B2 | 12/2009 | Cohen et al. |
| 7,878,030 B2 | 2/2011 | Burr |
| 8,214,007 B2 | 7/2012 | Baker et al. |
| 8,768,428 B2 | 7/2014 | Clare et al. |
| 2003/0083559 A1 | 5/2003 | Thompson |
| 2003/0109905 A1 | 6/2003 | Mok et al. |
| 2004/0073127 A1 | 4/2004 | Istvan et al. |
| 2005/0277841 A1 | 12/2005 | Shennib |
| 2007/0021689 A1 | 1/2007 | Stergiou et al. |
| 2007/0078324 A1 | 4/2007 | Wijisiriwardana |
| 2007/0255184 A1 | 11/2007 | Shennib |
| 2008/0139953 A1 | 6/2008 | Baker et al. |
| 2008/0287770 A1 | 11/2008 | Kurzweil et al. |
| 2008/0312708 A1 | 12/2008 | Snyder |
| 2009/0150113 A1 | 6/2009 | Kim et al. |
| 2009/0171233 A1 | 7/2009 | Lanfermann et al. |
| 2009/0299212 A1 | 12/2009 | Principe et al. |
| 2009/0326406 A1 | 12/2009 | Tan et al. |
| 2010/0069736 A1 | 3/2010 | Finneran et al. |
| 2010/0106044 A1 | 4/2010 | Linderman |
| 2010/0137749 A1 | 6/2010 | Jeong et al. |
| 2010/0137753 A1 | 6/2010 | Naldoni |
| 2010/0234699 A1 | 9/2010 | Lanfermann et al. |
| 2010/0234714 A1 | 9/2010 | Mercier et al. |
| 2010/0317958 A1 | 12/2010 | Beck et al. |
| 2012/0310069 A1 | 12/2012 | Clare et al. |

OTHER PUBLICATIONS

International search report and written opinion dated Sep. 7, 2012 for PCT Application No. US2012/40581.
Notice of allowance dated Feb. 21, 2014 for U.S. Appl. No. 13/486,257.
Office action dated Mar. 29, 2013 for U.S. Appl. No. 13/486,257.
Office action dated Dec. 5, 2012 for U.S. Appl. No. 13/486,257.
Standards for Reporting EMG Data. Dr. Roberto Merletti. Journal of Electromyography and Kinesiology. 1999.

SYSTEM AND METHOD FOR POWER-EFFICIENT TRANSMISSION OF EMG DATA

CROSS-REFERENCE TO RELATED APPLICATIONS

This application is a continuation of U.S. patent application Ser. No. 13/486,257, (now U.S. Pat. No. 8,768,428), filed Jun. 1, 2012, which claims the benefit of Provisional Application No. 61/492,136, filed on Jun. 1, 2011, the full disclosures of which are incorporated herein by reference.

BACKGROUND OF THE INVENTION

1. Field of the Invention

The present invention relates generally to systems and methods for medical monitoring and more particularly to a wireless system for collecting an electromyogram (EMG) signal and transmitting that signal to a hand-held device, such as a smart cell phone or other personal digital device having a display.

Neuromuscular feedback can be useful for muscle rehabilitation, relaxation, general conditioning, strengthening, and athletic training. In particular, surface electromyography (sEMG) uses skin-mounted electrodes to collect myoelectric signals associated with the contraction of a user's muscles. By placing an electrode patch over a muscle or a muscle group which is injured, which is being exercised to increase strength and/or performance, or which is in a state of hypercontraction, the activity of that muscle or muscle group can be monitored quantitatively. For example, a percentage of maximum effort can be monitored with a visual display provided to the user and/or trainer in order to optimize a rehabilitation or training protocol.

While such sEMG feedback offers great promise in both rehabilitation and training regimens, most sEMG equipment is relatively large, not portable, inconvenient to use, offers limited types of data, and requires significant energy consumption. It would thus be desirable to provide low energy consumption systems which are more convenient for the user and which minimally interfere with the training or other exercise or muscle control protocols. In particular, it would be desirable to provide monitoring systems employing an electrode patch which does not need to be wired to a remote unit for either powering or data collection. At least some of these objectives will be met by the inventions described herein.

2. Description of the Background Art

U.S. Pat. No. 5,277,197 describes a wearable exercise training system which monitors a muscle force signal (EMG) and provides feedback to the user. U.S. Pat. No. 4,811,742 describes a table top system for measuring EMG and stimulating muscle groups in response. U.S. Pat. No. 7,563,234 describes a rehabilitation system that exercises a body limb and measures EMG. Other patents and publications of interest include U.S. Pat. Nos. 5,722,420; 6,238,338; 6,440,067; 6,643,541; 6,984,208; 7,152,470; 7,359,750; 7,369,896; 7,602,301; 7,613,510; 7,628,750; 7,878,030; U.S. Publ. Nos. 2007/0021689; 2009/0150113; 2009/0171233; 2009/0326406; 2010/0106044; 2010/0137735; 2010/0137749; 2010/0234699; 2010/0234714. Commercial EMG systems are available from Noraxon USA, Inc., Scottsdale, Ariz. and Thought Technology Ltd., Quebec, Canada.

SUMMARY OF THE INVENTION

The present invention provides a system for monitoring and displaying muscle force data to a user. The system comprises a wearable patch or sensor unit which carries a pair of spaced-apart sensing electrodes and a ground electrode on a surface thereof. The patch is adapted to be secured to a patient's skin over a muscle group to be monitored with the electrodes in contact with the skin. Usually, the patch will have an adhesive surface for adhering to the skin, but straps, wraps, fitted clothing, tapes, and other conventional skin fasteners or compression aids could also be used.

The wearable patch or sensing unit will also carry circuitry needed to monitor a surface electromyogram (sEMG) signal present on the user's skin above the target muscle group, digitize the monitored (analog) signal, and wirelessly transmit the signal in the form which may be received by a remote monitor. Such wireless transmission will typically rely on digital transmission and may conveniently be implemented by a WiFi and/or a blue-tooth enabled personal communication or entertainment device having a display screen and capable of being programmed with software which can process the received signal and display the signal in a desired format. For example, the output may be displayed as a bar graph or other conventional data format (progress meter, line graph, pie graph, XY scatter chart, etc.) which provides an easy visual display of the effort being put forth by the user, typically as a percentage of maximum effort. Alternatively, the display device may be a dedicated hand-held, table mounted of other display unit intended for use primarily or only the patch device of the present invention.

Of particular interest to the present invention, the circuitry on the patch will be adapted to limit the power required to receive, digitize, process, and transmit the EMG signal to the remote display unit. The circuitry will typically include a limited bandwidth amplifier which receives signals from the electrodes and produces an analog output. An analog-to-digital converter receives and rectifies the analog output at a sample rate in the range from 3000 sec$^{-1}$ to 4000 sec$^{-1}$. The patch also carries a microprocessor which filters the digital signal from the converter to produce a smoothed output. In addition, a transmitter is provided on the patch which receives the output from the microprocessor and generates a wireless signal which can be transmitted to the display unit.

In particular aspects of the present invention, the sensing electrodes and/or ground electrode on the patch may be coated with silver chloride. The display unit may comprise a hand-held unit, such as a personal communicator or entertainment unit, for example an iPhone®, an iPad®, an iPod® Touch®, a Blackberry® phone, an Android® phone, or the like. The system of the present invention, however, is also compatible with laptop computers, desktop computers, and other conventional processors with display units having blue-tooth, WiFi, or other wireless reception capabilities. Still further, the display could be wall mounted, desktop mounted, or placeable anywhere it is accessible by the user, the physician, and or the patient.

In a further aspect of the present invention, a method for displaying muscle force data to a user comprises placing a patch on the user's skin over a muscle group to be monitored. The patch carries electrodes which engage the skin in order to sense EMG activity and produce a very low power analog electrical signal. The very low power electrical signal sensed by the electrodes is filtered and amplified with a limited bandwidth amplifier disposed on the patch. The filtered and amplified signal, in turn, is converted and rectified to produce a digital signal, where the conversion is at a rate in the range from 3000 sec$^{-1}$ to 4000 sec$^{-1}$. The digital signal is further filtered by a microprocessor on the patch to produce a smoothed output. The smoothed output is transmitted to a remote display unit (as described above) which receives and displays the smoothed output as a visual representation of the muscle activity being generated.

It has been found by the inventors herein that the sample rate from 3000 sec$^{-1}$ to 4000 sec$^{-1}$ provides sufficient samples to digitally filter the 400 Hz bandwidth after it is digitally rectified while still achieving rejection of most aliased artifacts. The numerical filter within the microprocessor then takes the rectified "spiked" signal and produces a smoothed, average signal using digital filtering set up from 0.5 Hz to 3 Hz. This approach both sums the data and averages the data to minimize the traffic and noise in the data collection and presentation. The signal may be resampled at 20 sec$^{-1}$ to capture muscle contractions so that as much data as possible can be delivered to the device and observed by the user with minimum energy consumption from the patch battery. It is important to note that not all raw data is delivered to the remote visual display. By appropriately filtering the data, only data necessary to provide a useful visual presentation of the muscle activity is provided. The system allows for the delivery of the filtered average of the raw data as "data packets" of 20 sec$^{-1}$ to the remote display device. By thus mathematically offsetting and suppressing unneeded data, a running cumulative average may be provided which is sufficient for the user while minimizing the energy consumption of the patch. Moreover, the integration of the filter, analog-to-digital converter, and the microprocessor allows for a further reduction in energy consumption.

Additionally, session data may be stored and evaluated separately for indication of muscle activity variance that may indicate risk of muscle fatigue. Data may be monitored for such deviations by comparison of sampled data over time to muscle calibration data. As muscle activity slopes downward in effectiveness over time, thresholds that correspond with muscle fatigue may be established. Once the threshold is reached, data may be delivered to the device and observed by the user to alert the user to potential for fatigue and a query for reduction or cessation of activity.

In use, the patch and system comprising the patch and a display unit allow muscle activity to be measured and filtered to provide useful data to users. In particular, the useful data comprises information on (1) which muscle is contracting, (2) when the target muscle is contracting, (3) how efficiently the target muscle is contracting, (4) indications or signs of muscle fatigue, (5) optionally providing a prompt or alert when the muscle may be worked harder to achieve a pre-determined goal, (6) optionally providing a prompt or alert when the muscle should be worked less to avoid injury or avoid exceeding a predetermined work pattern, and (7) prompt or alert when the user should relax and, as appropriate, recontract the muscle.

In other aspects of the present invention, the display unit may be used to adjust the filter bandwidth in the patch circuitry. For example, the bandwidth could be changed to increase or decrease the sensitivity or smoothness of the data output. Stroke and other patients with very low muscle activity would be able to decrease the filtering and increase sensitivity so that they can observe such low activity. Similarly, temperomandibular joint (TMJ) patients can adjust the sensitivity and filtering to be able to detect release of muscles surrounding the TMJ.

In yet other aspects of the present invention, the patch circuitry could be changed to transmit two data streams with the same and/or different levels of filtering, e.g., one with high frequency filtering and one with low frequency filtering. Transmitting two signals with the same filtering could service different electrode sensors on the patch The data streams could be sent selectively, simultaneously, or sequentially to the display. The ratio between the high frequency and low frequency filtered muscle activity signals can be an indicator of muscle fatigue.

DETAILED DESCRIPTION OF THE INVENTION

Figure 1:
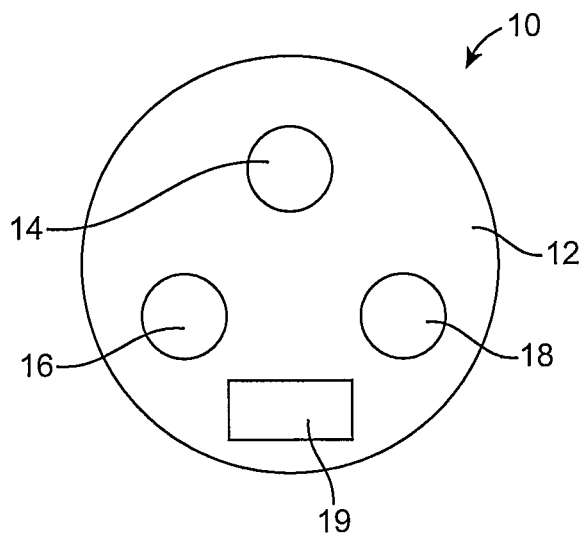
FIG. 1 illustrates an exemplary embodiment of a wearable patch placed on a user's quadriceps, constructed in accordance with the principles of the present invention. It should be noted that the patch may also be placed on a variety of other muscles and muscle groups which might be monitored.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

As illustrated in FIG. 1, a patch 10 according to the present invention will typically comprise a backing 12, a first sensing electrode 14, a second sensing electrode 16, and a ground electrode 18. The patch may optionally include further sensing and/or ground electrodes, but usually the pattern of three electrodes as illustrated will be sufficient. The patch 10 will also carry circuitry 19 to receive voltage from the electrodes 12, 14, convert the voltage to a digital signal, process the digital signal, and deliver the processed signal to a display unit 20 as described in detail below.

Figure 2:
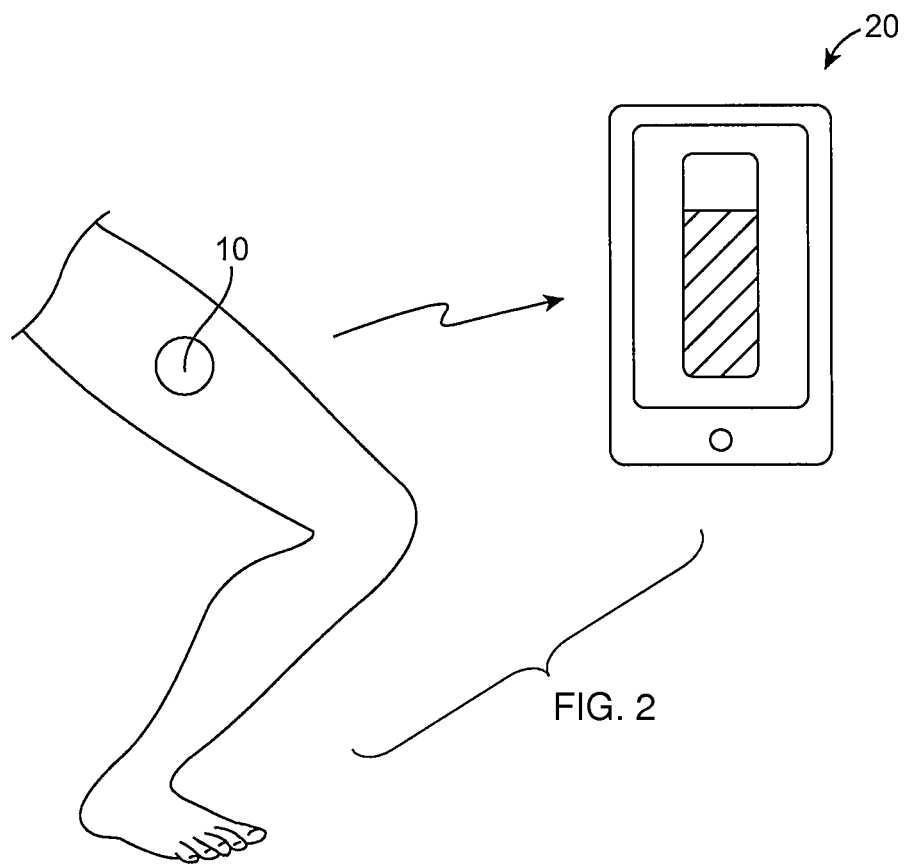
FIGS. 2 and 2A illustrate a system according to the present invention comprising a wearable patch and a display unit in the form of a personal communication device.

Referring now to FIG. 2, the patch 10 of the present invention will be worn on a user's skin over a target muscle or muscle group which is desired to be monitored. The patch 10 may be placed over any muscle group, e.g., as illustrated in the patient's upper leg. Patch 10 may be secured using adhesive placed on the same surface which carries the electrodes. Alternatively, straps, bandages, or other attachment mechanisms or devices could be utilized for holding the patch 10 in place. The system of the present invention will usually include at least a video display unit 20, typically a hand-held personal communication or entertainment unit of the type described above, and may include audio outputs as well. Alternatively, the display unit could provide just an alphanumeric output, but generally will be desirable to provide a visual display capable of presenting graphic as well as alphanumeric information to the user.

Figure 2A:
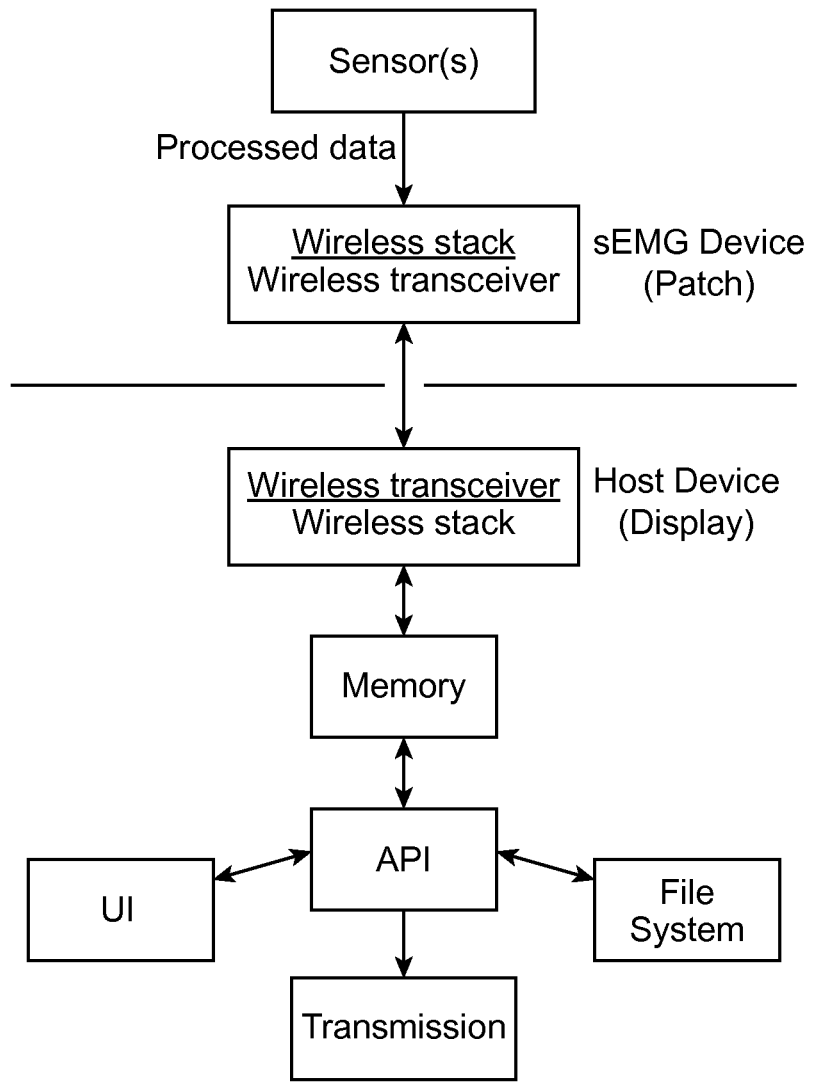
Figure 3A:
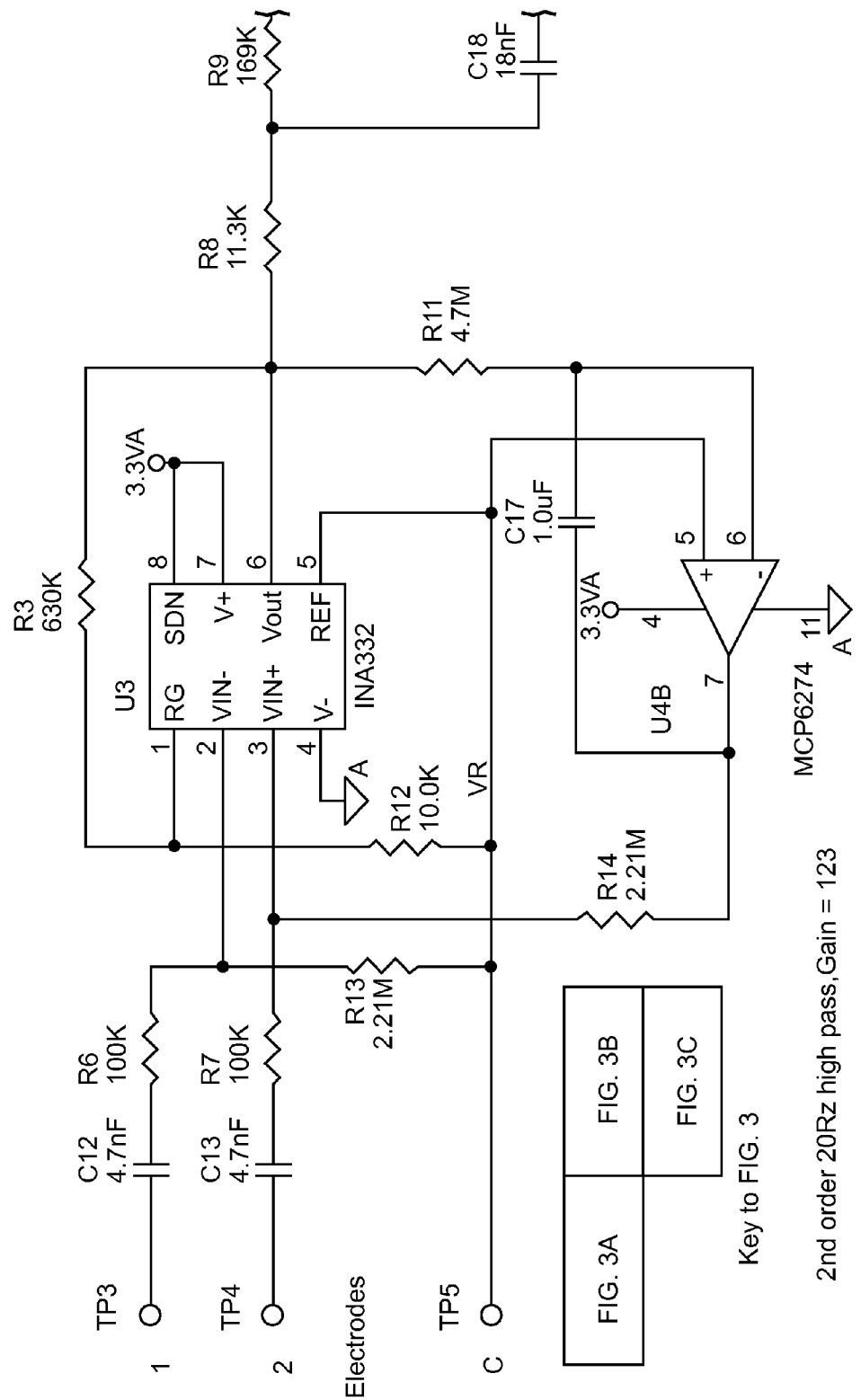
FIGS. 3A-3C and 4 through 7 illustrate circuitry which may be employed on the patch for collecting, filtering, and processing data according to the present invention.
Figure 3B:
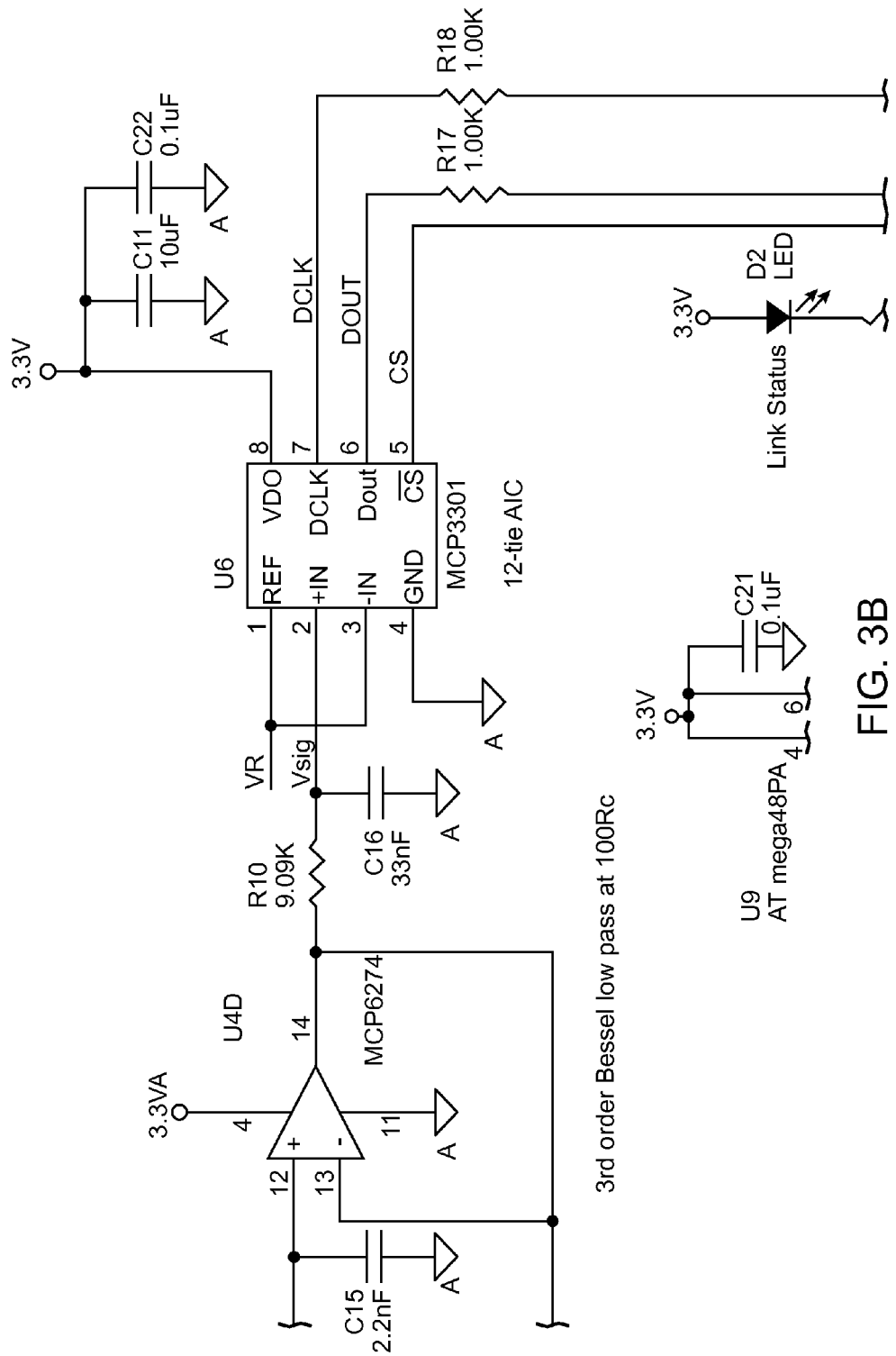
Figure 3C:
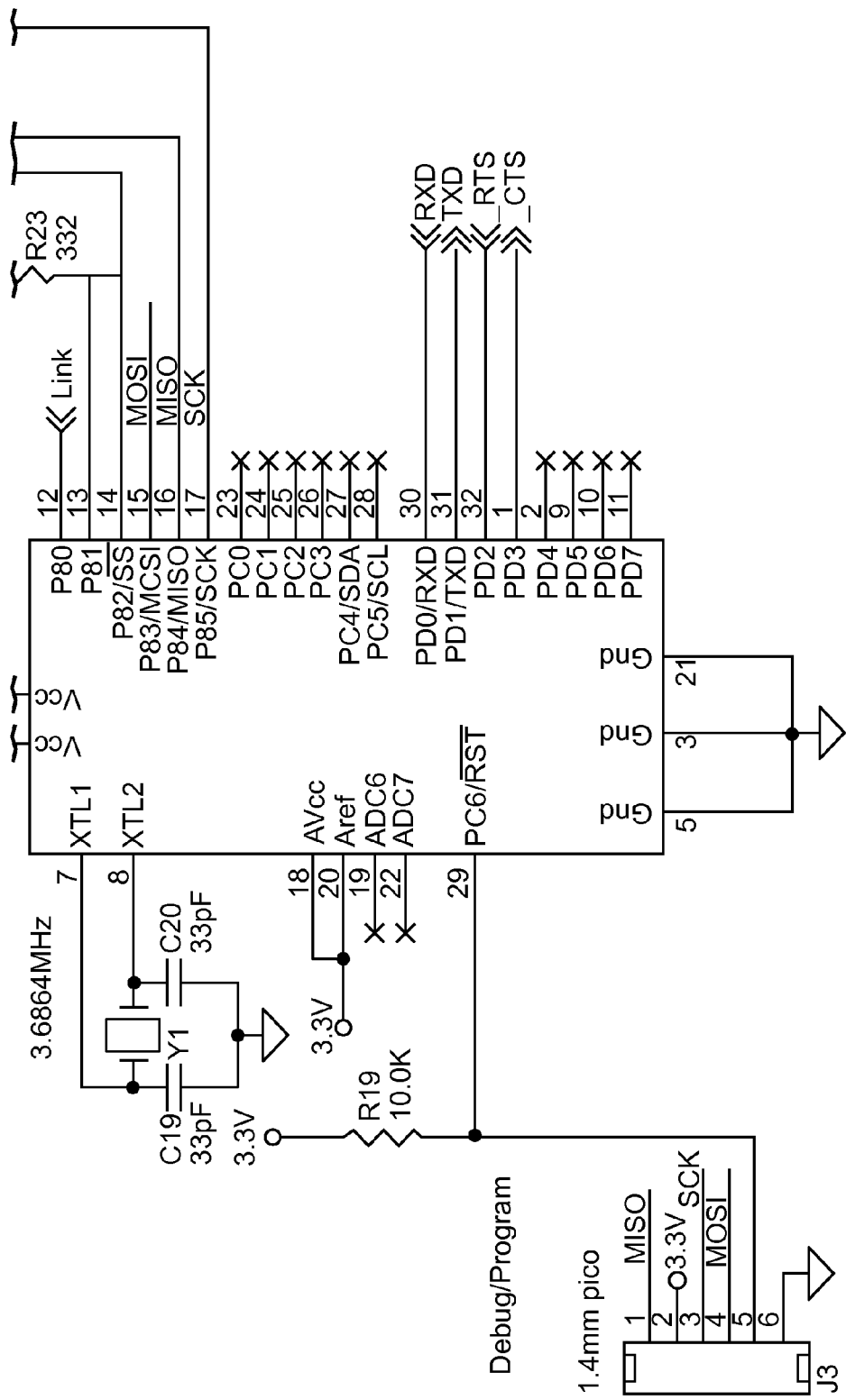
Figure 5:
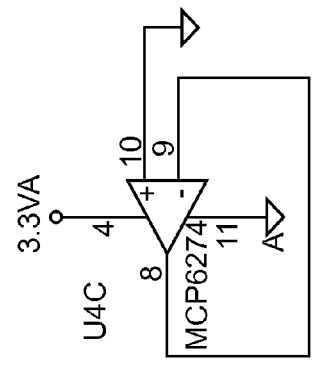
Figure 4:
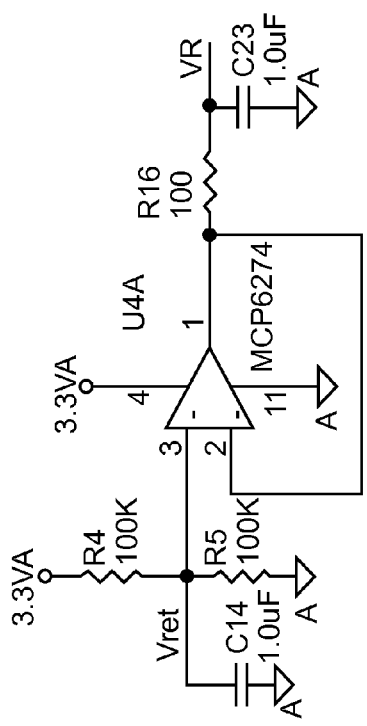
Figure 6:
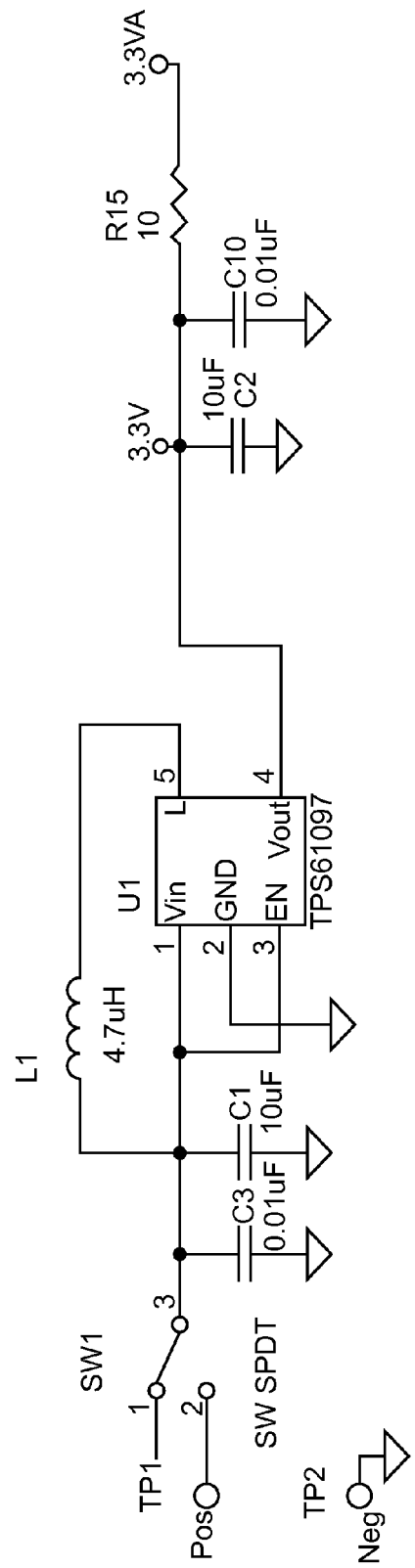
Figure 7:
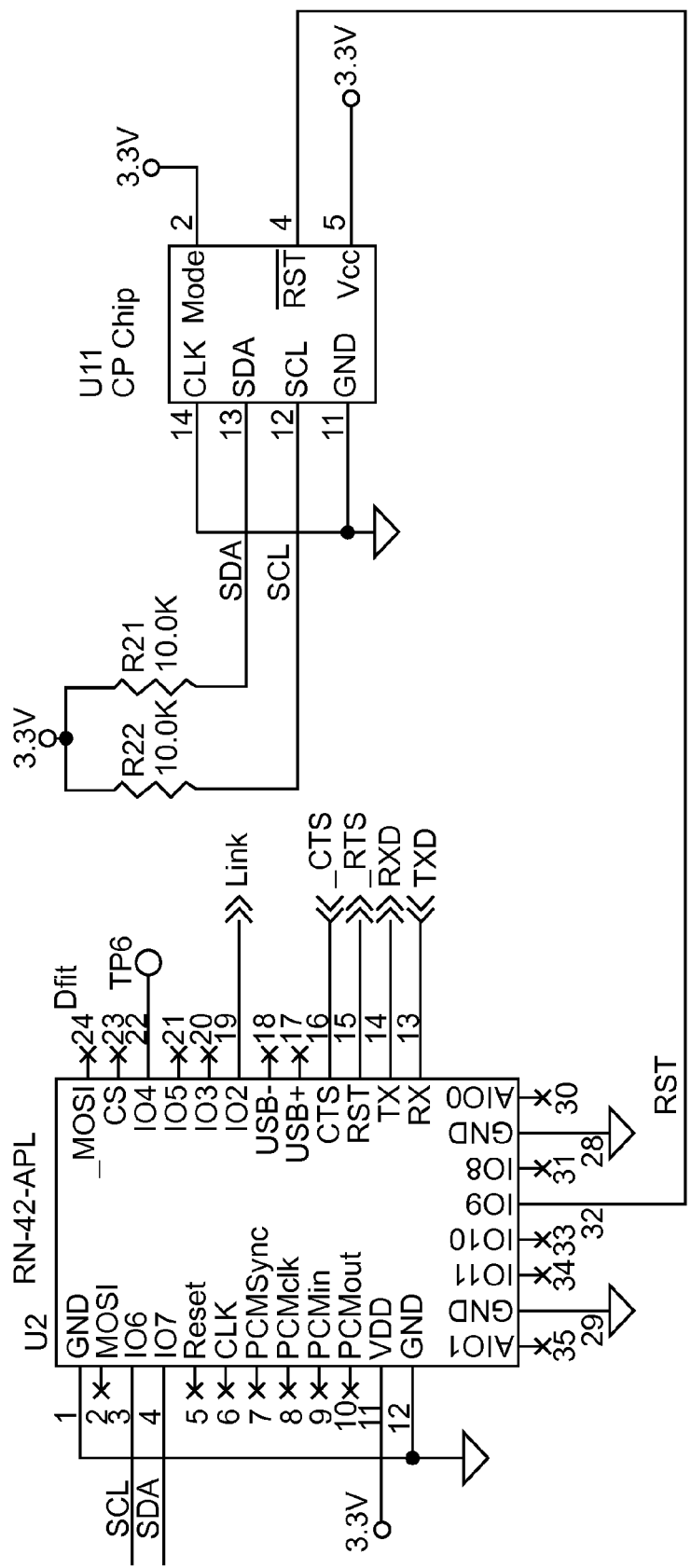

The system architecture can be understood with reference to FIG. 2A. The patch (sEMG device) includes the electrodes (sensors), circuitry to process the signal and data, and a wireless transceiver to communicate with a display (host device). The display also includes a wireless transceiver to communicate with the patch. In addition, the display includes memory, a user interface UI, a processing unit API, a file management system, and optionally a second transceiver for communicating with other units and/or the internet.

Detailed circuitry which may be used to implement the system and methods of the present invention is provided in FIGS. 3 through 7. The circuitry will provide the following operative components. A power supply typically includes a single-cell battery with a voltage from 0.9 V to 1.5 V in order to power the patch. The battery voltage is applied to a switch up converter (U1) to convert the battery voltage to a regulated 3.3 V supply for the electronics. This switching converter uses a variable width modulation to alternatively charge inductor L1 with current from the battery and then discharge the inductor through an internal diode to the energy storage capacitors C2 and C10. The pulse width is varied to maintain a constant voltage across these capacitors. The circuitry will typically also include a power switch, a power light or other indicator, a signal strength indicator, and a battery charge indicator.

A blue-tooth module U2 controls radio frequency (RF) communication with the remote display unit. Although blue tooth is shown, virtually any other low power wireless transceiver or wired connector could be used, e.g., USB, WiFi, ultrawide band, Z-wave, ANT, etc. The module U2 establishes a virtual serial connection that has bi-directional, asynchronous port RXD and TXD. Two signals, CTS and RTS, control the flow of data. A virtual link can be established either to a standard computer blue-tooth module or to a more specific communications bridge, such as those included in Apple® devices such as the iPhone® and the like. The blue-tooth module U2 manages communication with an Apple® specific security chip U11 that provides authentication when communicating with an Apple® product. Once the virtual link is established, further communication with the patch remains the same.

An Atmel® microprocessor U9 controls the acquisition and processing of data from the analog signal front end and responds to and sends data over the virtual link as required. The microprocessor is clocked at 3.6864 MHz to allow for exact division to 115 K Baud for serial communication. The microprocessor software is stored on an internal flash memory that is loaded with programming hardware from Atmel®. Other microprocessors could also be used.

A reference voltage VR is exactly half the 3.3 V power supply. Voltage divider R4 R5 creates a voltage that is buffered by U4A to provide a low impedance source that is connected to the patient through a reference electrode TP5. This same voltage provides a reference to the digital-to-analog converter DAC, U6. U4C is not used.

The electrode signal into the circuitry is applied differentially between TP3 and TP4. An instrumentation amplifier U3 amplifies the electrode signal and generates an output referenced to VR. The differential amplifier is combined with input capacitors C12 and C13, and an integrator formed by U4B, C17 and R11 works together to form a third order high pass active filter with a corner frequency of about 10 Hz. This signal is then applied to amplifier U4D that is configured as a third order, active low pass filter with a corner frequency of about 400 Hz that serves as an anti-alias filter for the system. Passive components R8, R9, C18, C15, R10 and C16 are part of this filter. The filtered analog signal is then applied to the digital-to-analog converter U6. Since the DC gain is one, the input to the digital-to-analog converter is also referenced to VR.

The digital-to-analog converter converts the voltage applied to its input pin 2 to a 13-bit result. If its input voltage is equal to VR, the output code generated is 0x1000 in HEX. One count lower is 0x0FFF and one count higher is 0x1001. The input is sampled when the control signal/Cs is brought low and the converted data is clocked out by DClk on the serial output DOUT. Since the numerical processing in U9 rectifies the differential encoded signal, the frequency is effectively doubled so that the 400 Hz input signal is handled as if were an 800 Hz signal. Thus, the sample frequency is set as 4000 $sec^{-1}$ to reduce the magnitude of alias frequencies to a reasonable level. Note that R17 and R18 are included to prevent the digital-to-analog converter from interfering with the microprocessor programming when the Pod is connected to the Atmel® programmer.

Further signal processing is performed by the microprocessor to convert the 400 Hz differential input into an average amplitude signal with 4 degrees of time response. This filtered signal is then sub-sampled at 20 $sec^{-1}$ and sent to the remote display for further interpretation and display.

Figure 8:
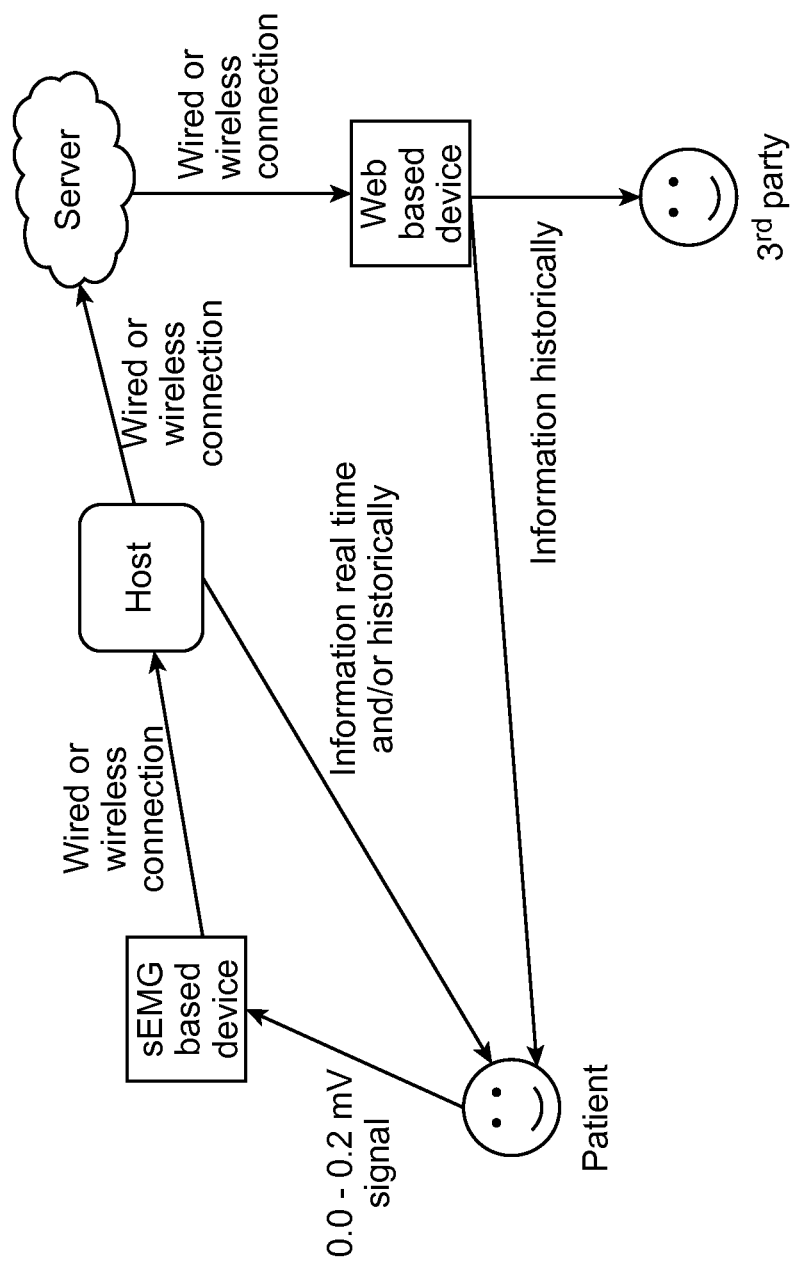
FIG. 8 illustrates a communication protocol for storing and sharing information acquired by the patch.

Referring now to FIG. 8, protocols for storing and transmitting data collected by the patch are shown:

1. The sEMG device (patch) measures a 0.0-0.2 mV signal from muscle of the patient through a skin mounted sensor.
2. The sEMG device (patch) transmits a converted, amplified, rectified and filtered signal wirelessly or via a hard wired connection to a host device.
3. The host device (display) displays the real time and historical signal to the user in selectable graphical formats. The host stores the results locally.
4. The host device can transmit stored results using any combination of wireless or wired connectivity supported by the device encrypted over the internet.
5. A cloud-based server receives the results and stores the data in a SQL database.
6. Another cloud based component runs a web server.
7. The web server can be accessed via any HTML enabled device.
8. Patients and third parties can compare and/or display historical information.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for displaying muscle force data to a user, said method comprising: placing a patch on the user's skin over a muscle group to be monitored, wherein electrodes on the patch engage the skin, wherein the electrodes sense electromyographic (EMG) activity and produce an analog electrical signal; filtering and amplifying the analog electrical signal with a limited bandwidth amplifier on the patch, wherein the analog signal is rectified and filtered to produce a digital signal and the resulting digital signal sampled at a rate in range from 3000 sec-1 to 4000 sec-1 to produce an output having an averaged amplitude on a microprocessor; converting and rectifying the filtered and amplified analog signal to produce a digital signal; processing the distal signal in a microprocessor on the patch to produce a smoothed output, wherein the microprocessor sub-samples the output having an averaged amplitude to produce a sub-sampled output; transmitting the smoothed output; receiving and displaying the smoothed output on a remote display unit.

2. A method as in claim 1, wherein the smoothed output is displayed on a remote video and/or audio unit.

3. A method as in claim 2, wherein the display unit is hand-held.

4. A method as in claim 1, wherein the patch has a pair of spaced-apart sensing electrodes and a ground electrode on a surface thereof.

5. A method as in claim 1, wherein a transmitter which receives the sub-sampled output from the microprocessor and produces a wireless signal which is transmitted to the remote display unit.

6. A method as in claim 1, wherein the electrodes are coated with silver chloride.

7. A method as in claim 1, wherein the surface of the patch is covered with an adhesive.

8. A method as in claim 1, wherein the hand-held unit is a personal communication or entertainment unit having a wireless receiver.

9. A method as in claim 1, wherein filtering and amplifying the analog electrical signal with a limited bandwidth amplifier on the patch produces two data streams with the same and/or different levels of filtering.

10. A method as in claim 9, wherein one data stream is produced by high frequency filtering and another data stream is produced by low frequency filtering, wherein a ratio between the high frequency filtered muscle activity signal and a low frequency filtered muscle activity provides an indicator of muscle fatigue.

11. A method as in claim 9, wherein the two signals are obtained from different electrode sensors on the patch and treated with the same filtering.

12. A method as in claim 9, wherein the data streams are sent selectively, simultaneously, or sequentially to the display.

13. A method as in claim 9, further comprising obtaining and displaying at least one of the following data:
- how long the target muscle is contracting;
- how many times the target muscle contracts;
- how efficiently the target muscle is contracting; and
- indications or signs of muscle fatigue.

14. A method as in claim 9, further comprising providing a prompt upon the occurrence of at least one of the following events:
- when the muscle may be worked harder to achieve a predetermined goal;
- when the muscle should be worked less to avoid injury or to avoid exceeding a predetermined work pattern;
- when the user should relax and, as appropriate and re-contract the muscle;
- when specified number of repetitions is achieved in a session; and
- when a session or user specified number of sessions are not completed within definable time periods.

15. A method as in claim 9, further comprising comparing two signals with same level of filtering used for analysis of bilateral or contralateral symmetry.

* * * * *